United States Patent
Gomez

(10) Patent No.: US 12,303,585 B2
(45) Date of Patent: May 20, 2025

(54) MEDICINAL MUSHROOM-BASED TOPICAL COMPOSITION

(71) Applicant: Cynthia Gomez, Denver, CO (US)

(72) Inventor: Cynthia Gomez, Denver, CO (US)

( * ) Notice: Subject to any disclaimer, the term of this patent is extended or adjusted under 35 U.S.C. 154(b) by 0 days.

(21) Appl. No.: 18/911,447

(22) Filed: Oct. 10, 2024

(65) Prior Publication Data

US 2025/0032399 A1    Jan. 30, 2025

Related U.S. Application Data

(63) Continuation of application No. 18/615,128, filed on Mar. 25, 2024.

(60) Provisional application No. 63/455,558, filed on Mar. 30, 2023.

(51) Int. Cl.
| | | |
|---|---|---|
| A61K 36/00 | (2006.01) |
| A61K 8/67 | (2006.01) |
| A61K 8/92 | (2006.01) |
| A61K 8/9728 | (2017.01) |
| A61K 8/9794 | (2017.01) |
| A61Q 17/04 | (2006.01) |
| A61Q 19/00 | (2006.01) |

(52) U.S. Cl.
CPC ............ *A61K 8/9728* (2017.08); *A61K 8/671* (2013.01); *A61K 8/676* (2013.01); *A61K 8/92* (2013.01); *A61K 8/9794* (2017.08); *A61Q 17/04* (2013.01); *A61Q 19/00* (2013.01)

(58) Field of Classification Search
CPC .................................... A61K 8/9728
See application file for complete search history.

*Primary Examiner* — Qiuwen Mi

(74) *Attorney, Agent, or Firm* — Colorado Venture Patents LLC

(57) ABSTRACT

A topical composition for tattooed skin combines medicinal mushroom extracts (Chaga, Lion's Mane, Turkey Tail and Reishi) with either aloe vera gel or non-comedogenic carrier oils. The formulation promotes rapid healing, reduces infection risk, and provides UV protection for long-term tattoo preservation. The composition addresses shortcomings of existing aftercare products by preventing over-moisturization and clogged pores while offering UV protection. Suitable for all skin types, the hypoallergenic formulation can be applied to both fresh and aging tattoos, ensuring optimal skin health and tattoo vibrancy throughout the tattoo's lifetime.

8 Claims, 4 Drawing Sheets

Shea Butter     Synthetic Beeswax Pellets     Sweet Almond Oil

Grape seed Oil     Mushroom Extract

Aloe vera gel mixture  Red Reishi incture

Turkey Tail tincture  Chaga tincture

MEDICINAL MUSHROOM-BASED TOPICAL COMPOSITION

CROSS-REFERENCE TO RELATED APPLICATIONS

This application claims the benefit of U.S. provisional Patent Application 63/455,558 filed on Mar. 30, 2023, and U.S. Non-provisional patent application Ser. No. 18/615,128 filed on Mar. 25, 2024, the entire contents of which are hereby incorporated by reference.

FIELD OF THE INVENTION

The present invention pertains to the field of dermatological skincare, specifically to the formulation of topical products designed for the care and maintenance of tattooed skin. It falls within the realm of cosmetic and therapeutic skin treatments that aim to enhance the healing of the epidermis following the trauma induced by tattooing procedures. The field also encompasses the development of aftercare lotions, salves, gels, tattoo glides and other topical applications that incorporate bioactive compounds for improved skin healing and tattoo preservation.

BACKGROUND OF THE INVENTION

Traditional methods for tattoo aftercare have predominantly involved the use of mild soaps for cleansing and unscented moisturizers to hydrate the skin throughout the healing phases. However, these conventional products lack specific ingredients that actively contribute to the skin's natural healing processes. Moreover, the tattoo industry has commonly recommended petroleum-based products, such as Aquaphor, which have been found to be counterproductive. These products tend to over-moisturize scabs due to their slow absorption rate, potentially leading to clogged pores and a complicated healing process.

The over-moisturization of tattooed skin can create an environment that is conducive to bacterial growth, increasing the risk of infection and potentially leading to longer healing times and compromised tattoo quality. The occlusive nature of petroleum-based products can trap bacteria and other contaminants against the skin, which is particularly problematic during the critical initial healing stages when the skin is most vulnerable. This can increase the risk of infection and potentially leading to longer healing times and compromised tattoo quality.

Additionally, the use of these heavy, occlusive products often results in a lack of breathability for the skin. This can delay the natural cell turnover and oxygenation processes that are essential for proper wound healing. As a result, the tattooed area may experience increased itchiness, irritation, blistering, rough scabbing and discomfort, which can tempt individuals to scratch or pick at the healing tattoo, further risking damage and infection.

Another significant issue with current aftercare products is their failure to address the long-term care of the tattoo. While initial healing is crucial, the maintenance of tattoo vibrancy and clarity over time is often overlooked. Exposure to ultraviolet (UV) radiation can cause tattoos to fade prematurely, and most aftercare products do not offer any protection against these harmful rays. Most aftercare products currently on the market claim increased vibrancy of a tattoo, however the perceived benefit is generally only temporary while the skin is hydrated immediately following application of such tattoo aftercare products. Such products typically do nothing to actually help protect the skin and retain vibrancy as a tattoo ages.

Furthermore, many individuals with sensitive skin or allergies find that the limited selection of aftercare products available cannot meet their needs. The use of synthetic fragrances, preservatives, and other potential irritants in aftercare products can lead to allergic reactions, exacerbating the challenges of healing and maintaining a tattoo.

In the tattoo industry, there is a critical need for aftercare products that contain ingredients specifically designed to aid in tattoo healing. Current products on the market, including popular brands, often lack active ingredients that directly contribute to the healing process. The distinction between these products and common body lotions is primarily in their marketing and target audience, rather than in their formulation or efficacy for tattoo aftercare.

Moreover, there is a notable absence of tattoo aftercare products that offer UV protection for freshly tattooed skin. While protecting a new tattoo from sun exposure is essential, applying traditional sunscreens to a fresh tattoo is not recommended due to the chemicals present, which can negatively affect the healing process. This creates a paradoxical situation where protecting the tattoo from UV damage is necessary, but conventional methods of UV protection are unsuitable.

Lastly, some recommended tattoo aftercare products are comedogenic or create a thick, impermeable barrier over the new tattoo. This barrier can block oxygen, which is crucial for the wound healing process, potentially delaying or even hindering the body's natural healing capabilities.

In light of these issues, there is a clear need for an aftercare product that not only aids in the efficient and effective healing of the tattooed skin but also supports the long-term health and appearance of the tattoo. Such a product should address the challenges of infection prevention, inflammation reduction, and UV protection while ensuring proper breathability and avoiding the use of potential irritants.

SUMMARY OF THE INVENTION

An embodiment of the invention presents a novel approach to tattoo aftercare by introducing a unique formulation that synergistically combines the therapeutic properties of medicinal mushroom extracts, specifically Chaga, Lion's Mane, Turkey Tail and Reishi, with the soothing effects of aloe vera gel and non-comedogenic carrier oils. This innovative blend addresses common issues associated with traditional aftercare products, such as pore-clogging and delayed healing, while enhancing the body's immune response and expediting the natural healing process.

The selected medicinal mushroom extracts are renowned for their wound-healing capabilities, attributed to their ability to stimulate immune epithelial cells, support the extracellular matrix, and modulate cytokines, growth factors, and inflammatory intermediates. The formulation is designed to promote rapid healing, reduce the risk of infection, and maintain tattoo vibrancy by providing UV protection. The high melanin content found in Chaga mushroom extract offers an additional advantage by providing a natural layer of UV radiation protection, which aids in maintaining the tattoo's vibrancy and preventing premature fading due to sun exposure.

An embodiment of the invention represents a significant advancement in tattoo aftercare by addressing the shortcomings of existing products. It eliminates the risk of over-moisturization and clogged pores often associated with petroleum-based products and fills the gap in the market for a product that offers long-term protection against UV radiation. The formulation is designed to be safe for all skin types, non-toxic, and hypoallergenic, minimizing the likelihood of adverse reactions. The composition is recommended for both fresh and aging tattoos, ensuring that the skin remains vibrant, healthy, and well-protected throughout the life of the tattoo.

Embodiments of the invention provide a comprehensive solution that promotes healing, preserves tattoo quality, and enhances overall skin health, addressing the problems of ineffective healing ingredients in current products, the risk of over-moisturization, and the lack of long-term tattoo protection from UV rays.

DETAILED DESCRIPTION

Figure 1:
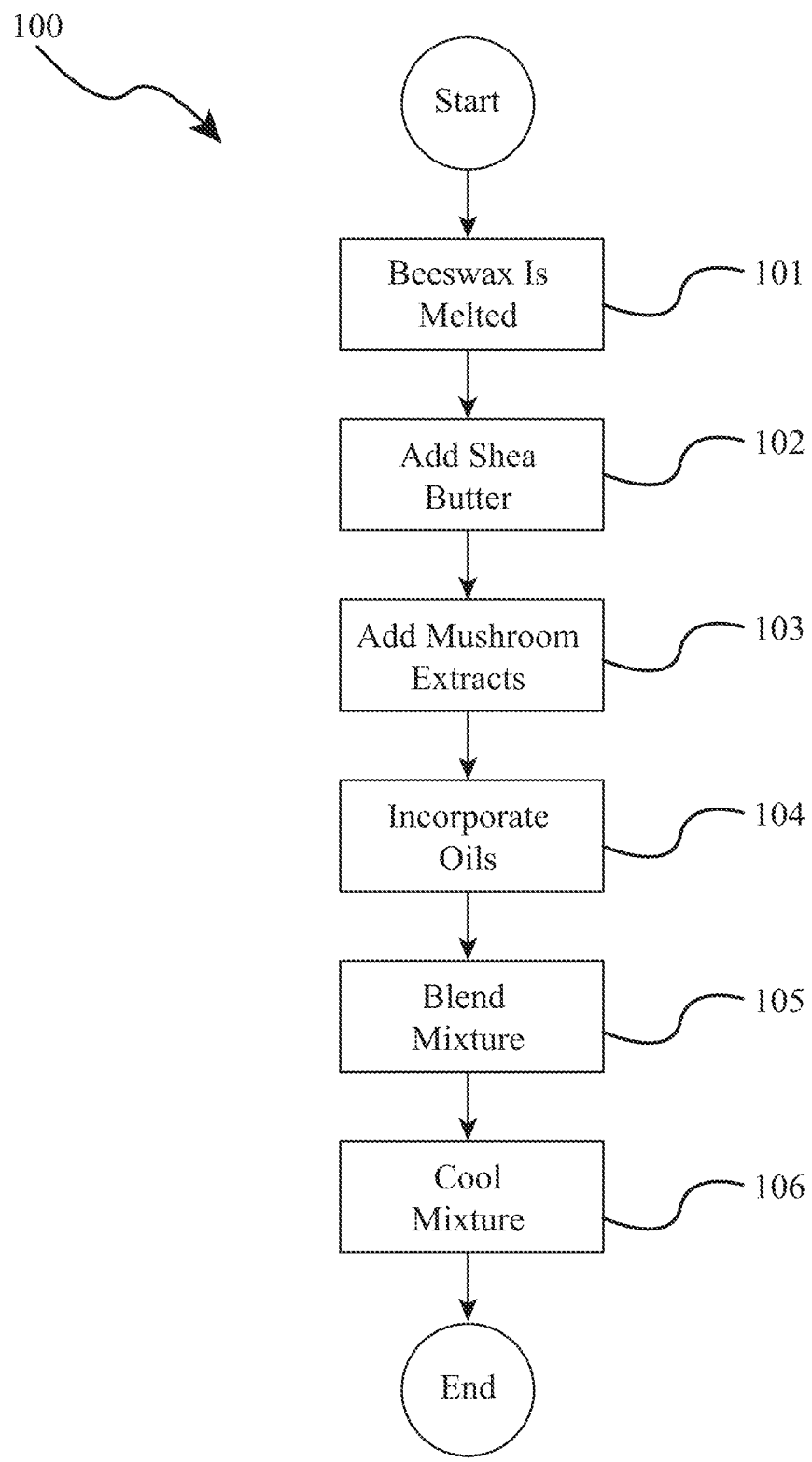
FIG. 1 depicts a flowchart illustrating the preparation process for the tattoo glide composition in an embodiment.
Figure 2:
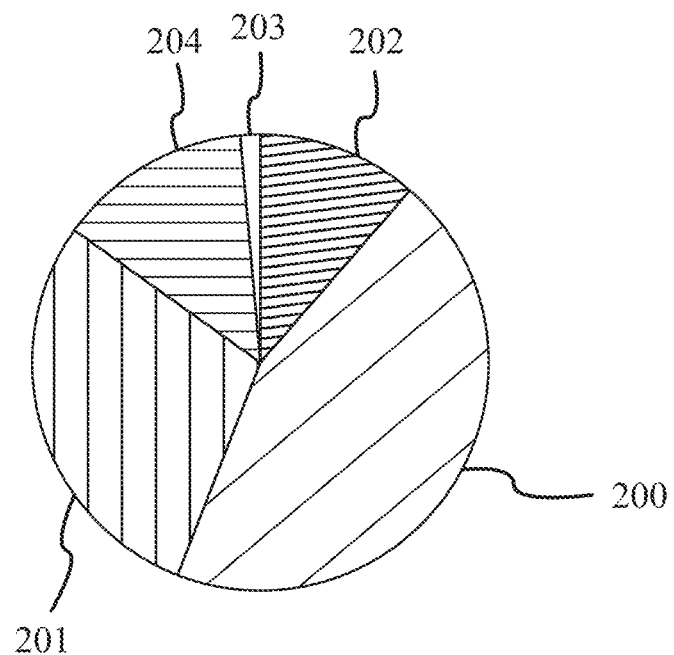
FIG. 2 depicts a pie chart depicting the percentage composition of ingredients used in a topical formulation in an embodiment.
Figure 2:
Figure 2:
Figure 2:
Figure 2:
Figure 2:
Figure 3:
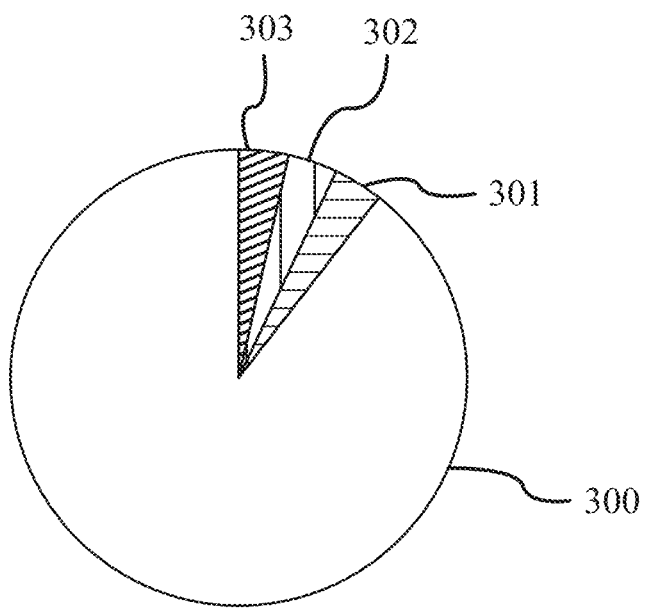
FIG. 3 depicts a pie chart illustrating the composition of a gel formulation in an embodiment.
Figure 3:
Figure 3:
Figure 3:
Figure 3:
Figure 4:
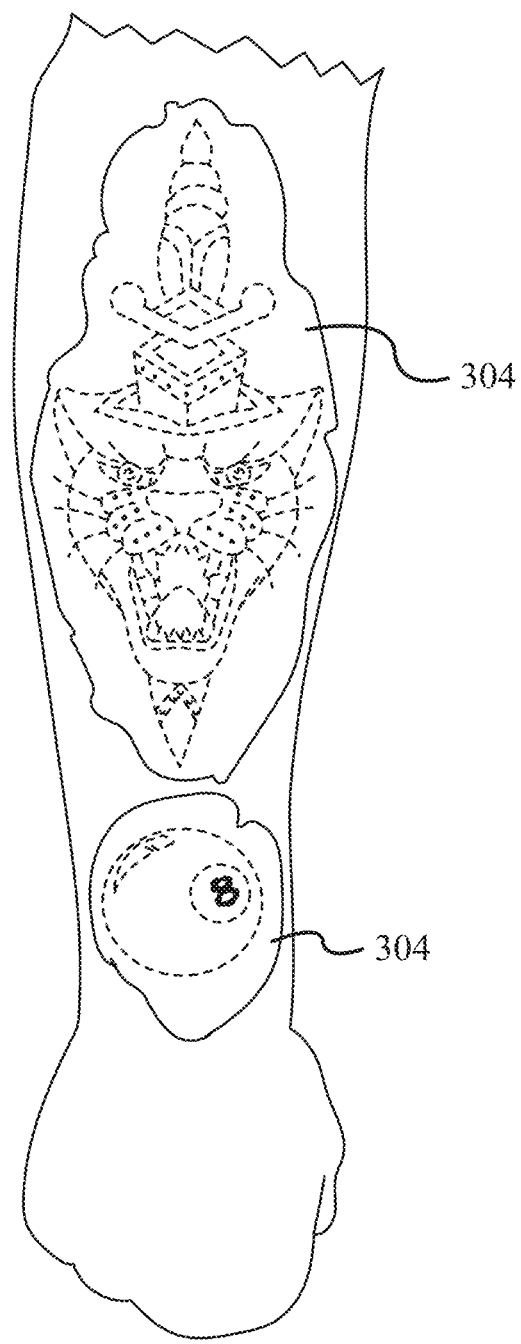
FIG. 4 depicts an exemplary use of an embodiment placed upon tattooed skin during aftercare.

An embodiment of the present invention provides a novel approach to tattoo aftercare by introducing a unique formulation that synergistically combines the therapeutic properties of medicinal mushroom extracts 203 with the soothing effects of aloe vera gel 300 and the safety of non-comedogenic carrier oils. This innovative blend not only circumvents the common issues associated with traditional aftercare products, such as pore-clogging and delayed healing, but it also enhances the body's immune response, thereby expediting the natural healing process.

At the core of an embodiment of the present invention lies a carefully selected combination of medicinal mushrooms, specifically Chaga, Lion's Mane, Turkey Tail and Reishi, which are renowned for their wound-healing capabilities. These mushrooms are rich in bioactive compounds such as beta-glucans, polysaccharides, and antioxidants, which contribute to their ability to stimulate immune epithelial cells, support the extracellular matrix, and modulate cytokines, growth factors, and various inflammatory intermediates. The formulation leverages these properties to create a comprehensive solution that addresses both the immediate needs of newly tattooed skin and the long-term maintenance of tattoo vibrancy and skin health.

This topical aftercare composition in an embodiment of the present invention is designed to promote rapid healing, reduce the risk of infection, and maintain the clarity and vibrancy of tattoos by providing UV protection. The inclusion of aloe vera gel 300 serves as a hydrating and soothing agent, while the non-comedogenic carrier oils ensure that the skin can breathe properly during the healing process. This careful balance of ingredients creates a product that is not only effective but also suitable for all skin types, being hypoallergenic and non-irritating.

An embodiment of the present invention is specifically formulated to address the unique challenges associated with tattoo aftercare. The composition is designed to promote rapid healing, prevent infection, and maintain tattoo vibrancy through a carefully selected blend of medicinal mushroom extracts 203, aloe vera gel 300, and non-comedogenic carrier oils.

The formulation in an embodiment leverages the synergistic effects of Chaga, Lion's Mane, Turkey Tail and Reishi mushroom extracts 203, each chosen for their specific healing properties. Formulations in embodiments of the invention comprise mushroom extracts 203 such as Shiitake, Cordyceps, Maitake, Agaricus Blazei, Oyster, Porcini, Enoki, Matsutake, Wood Ear, King Trumpet, and White Button, each selected for their unique healing, anti-inflammatory, antimicrobial, and antioxidant properties that can contribute to tattoo aftercare and skin health.

Chaga mushrooms, rich in antioxidants such as polyphenols, flavonoids, and melanin, help protect the tattooed skin from oxidative stress and environmental pollutants. This protection is crucial during the initial healing phase when the skin is most vulnerable.

Lion's Mane mushrooms contribute neuroprotective and anti-inflammatory properties, which can aid in pain management and reduce swelling and redness associated with the tattooing process. Reishi mushrooms provide immune-boosting and anti-inflammatory effects, supporting the body's natural healing processes and reducing the risk of infection.

Turkey Tail (*Trametes versicolor*) is a medicinal mushroom that offers significant benefits in the context of an embodiment of the invention. As part of the synergistic blend of mushroom extracts 203, Turkey Tail contributes to the formulation's wound-healing, immune-boosting, and antioxidant properties in an embodiment. Turkey Tail contains polysaccharides, including protein-bound PSP and $\beta$-1,3 and $\beta$-1,4 glucans, which are known to stimulate immune epithelial cells, support the extracellular matrix, and modulate cytokines and growth factors. These compounds enhance the body's natural healing processes, potentially reducing inflammation and healing time for tattooed skin. Additionally, Turkey Tail's high antioxidant content, particularly when extracted with methanol, can help protect the tattooed skin from oxidative stress and environmental pollutants, contributing to long-term tattoo preservation. The mushroom's antibacterial properties against common pathogens like *Staphylococcus aureus* and *Escherichia coli* further support its role in reducing the risk of infection in newly tattooed skin. Moreover, Turkey Tail's potential antiviral and antifungal actions provide additional protection during the critical healing phase in accordance with embodiments. By incorporating Turkey Tail extract into the tattoo aftercare formulation, the invention leverages these multiple beneficial properties to promote rapid healing, reduce infection risk, and support long-term skin health and tattoo vibrancy. As part of the synergistic blend of mushroom extracts 203, Turkey Tail contributes to the formulation's wound-healing, immune-boosting, and antioxidant properties in an embodiment.

Shiitake mushrooms contain compounds with potent anti-inflammatory and antimicrobial properties. In the context of an embodiment, these properties can help reduce inflammation in the tattooed area while fighting off harmful bacteria on the skin. The antimicrobial action of shiitake extract contributes to preventing infections during the critical healing phase of a new tattoo.

Cordyceps mushrooms are notable for their wound healing properties, which can promote faster healing of tattooed skin. This is particularly beneficial as tattoos essentially create an open wound in the skin. Additionally, cordyceps possess anti-inflammatory and antimicrobial properties that can help reduce inflammation in the skin and fight off bacteria, further supporting the healing process and protecting against potential infections in the tattooed area in accordance with an embodiment.

Maitake mushrooms offer significant anti-inflammatory properties beneficial in tattoo aftercare in accordance with an embodiment. When incorporated into the formulation in an exemplary embodiment, maitake extract can help reduce inflammation and redness in the tattooed area, promoting a smoother and potentially faster healing process. This anti-inflammatory action contributes to minimizing discomfort and swelling associated with fresh tattoos in accordance with an embodiment.

Agaricus Blazei mushrooms are known for their strong antimicrobial properties. In the context of tattoo aftercare in accordance with an embodiment, extracts from this mushroom help protect the skin from infections during the healing process. This protective action is crucial in the days following the tattooing procedure in accordance with an embodiment of the invention when the skin is most vulnerable to bacterial invasion.

Oyster mushrooms contribute anti-inflammatory properties to the tattoo aftercare formulation in accordance with an embodiment. These properties can help reduce inflammation and promote healing of the tattooed skin. By potentially decreasing swelling and redness, oyster mushroom extract may contribute to a more comfortable healing experience and support the overall health of the tattooed skin.

Porcini mushrooms are rich in antioxidants, making them a beneficial addition to the tattoo aftercare formulation in accordance with an embodiment. These antioxidants can help protect the skin from damage caused by free radicals and environmental stressors. In the context of tattoo care, this protective action may contribute to maintaining the overall health of the tattooed skin and potentially preserving the vibrancy of the tattoo over time.

Enoki mushrooms are known for their high antioxidant content. When incorporated into the tattoo aftercare formulation in accordance with an embodiment, enoki extract promotes skin health and healing after getting a tattoo. The antioxidants may assist in neutralizing free radicals, potentially reducing oxidative stress on the skin during the healing process and supporting long-term skin health in the tattooed area.

Matsutake mushrooms possess anti-inflammatory properties that can be beneficial in tattoo aftercare in accordance with an embodiment. When included in the formulation in accordance with an embodiment, matsutake extract can help reduce redness and swelling in the tattooed area, promoting healing. This anti-inflammatory action contributes to a more comfortable recovery period and potentially support faster healing of the tattooed skin in an embodiment.

Wood ear mushrooms offer anti-inflammatory properties that can be valuable in tattoo aftercare. When incorporated into the formulation in accordance with an embodiment, wood ear extract can help soothe and calm the skin during the tattoo healing process. This calming effect may help reduce irritation and discomfort associated with healing tattoos, potentially supporting a smoother recovery.

King Trumpet mushrooms are known for their antimicrobial properties. In the context of tattoo aftercare in accordance with an embodiment, extracts from this mushroom help protect the skin from infections while the tattoo heals. This protective action is particularly important during the initial healing phase when the skin is most susceptible to bacterial contamination.

White button mushrooms contribute anti-inflammatory properties to the tattoo aftercare formulation in accordance with an embodiment of the invention. These properties can help reduce inflammation in the tattooed area and promote healing. By decreasing swelling and redness, white button mushroom extract may support a more comfortable healing process and contribute to the overall health of the tattooed skin.

In accordance with various embodiments of the invention, the mushrooms incorporated into the formulation are freeze-dried prior to inclusion within the formulation. The freeze-dry method for dehydrating mushrooms in preparation for inclusion in a formulation in accordance with an embodiment of the invention involves a process known as lyophilization. This method begins by freezing the mushrooms at a very low temperature, typically below −40° C. The rapid freezing creates small ice crystals within the mushroom structure, which helps preserve its cellular integrity.

In alternative embodiments, as an alternative to or in addition to freeze-drying methods, more conventional dehydration methods can be used to dehydrate the mushroom in embodiments of the invention. While the freeze-drying method are recognized by the inventor to provide optimal preservation of bioactive compounds, alternative dehydration methods may also be employed in the preparation of medicinal mushroom extracts. These methods may include air-drying, oven-drying, or sun-drying. Although these traditional dehydration techniques may result in some loss of heat-sensitive compounds, they can still yield effective extracts suitable for incorporation into the formulation. The choice of dehydration method may be based on factors such as cost-effectiveness, equipment availability, or production scale in accordance with embodiments of the invention. Regardless of the dehydration method used, the subsequent extraction process remains consistent to ensure a comprehensive capture of beneficial compounds from the mushroom species. The final product's efficacy may vary slightly depending on the dehydration method employed in accordance with various embodiments, but the core therapeutic benefits of the medicinal mushrooms are retained in the composition.

Once frozen, the mushrooms are placed in a vacuum chamber in accordance with the formulation in an embodiment. Under these low-pressure conditions, the ice crystals in the mushrooms undergo sublimation—a process where the ice turns directly into vapor without passing through the liquid phase. This sublimation process removes the moisture content from the mushrooms while maintaining their structure and nutrient profile.

The freeze-drying process typically occurs in two main stages. During the primary drying stage, about 95% of the water content is removed. The chamber pressure is lowered, and heat is slowly introduced to facilitate sublimation. The temperature is carefully controlled to remain below the mushrooms' collapse temperature. In the secondary drying stage, the remaining bound water molecules are removed. The temperature is raised higher than in the primary drying stage, but still kept below levels that could damage the mushrooms' bioactive compounds.

The entire freeze-drying process can take anywhere from 24 to 72 hours, depending on the mushroom type, size, and quantity being processed. This method of dehydration offers several advantages for preparing mushrooms for inclusion in tattoo aftercare formulations.

The low-temperature process helps preserve delicate vitamins, minerals, and bioactive compounds in the mushrooms, ensuring their therapeutic properties remain intact in accordance with the formulation in an embodiment of the invention. Freeze-drying maintains the mushrooms' cellular structure, which can be beneficial for extraction processes and the overall efficacy of the final product. The removal of moisture through freeze-drying significantly extends the shelf life of the mushrooms, reducing the risk of spoilage and maintaining their potency over time. Additionally, freeze-dried mushrooms are lightweight and have a lower volume compared to fresh mushrooms, making them easier to store, transport, and incorporate into various formulations.

The method for preparing a tattoo care composition involves several key steps in accordance with various embodiments, each designed to maximize the therapeutic benefits of the medicinal mushrooms while ensuring a stable and consistent formulation.

By utilizing the freeze-dry method, the embodiment ensures that the medicinal mushroom extracts 203 retain their maximum therapeutic potential for inclusion in the tattoo glide formulation and/or the tattoo aftercare formulation in accordance with various embodiments. This process helps preserve the anti-inflammatory, antimicrobial, and antioxidant properties of the mushrooms, which are crucial for promoting healing and protecting the tattooed skin, and delivering various benefits associated with embodiments of the invention during intended uses.

Following freeze-drying, in accordance with an embodiment the mushrooms undergo a dual-phase extraction method to obtain the medicinal compounds. This process involves both hot water and ethanol extractions to ensure a full spectrum of healing compounds is captured from each mushroom species. The extraction process begins with a careful selection of high-quality mushrooms, which are then prepared for extraction. The first phase involves soaking finely ground mushrooms in high-proof grain alcohol for several weeks. The second phase involves boiling the alcohol-extracted mushrooms in hot water for several hours. Once both extractions are complete, the alcohol and water extracts are combined to create a potent extract containing a wide range of beneficial compounds from the mushrooms.

The emulsification process differs for the salve and gel formulations in accordance with embodiments. For the salve formulation, the carrier oils, waxes, and butters are gently heated and slowly combined to create a uniform base. The mushroom extracts 203, vitamins, emollients, emulsifiers, and stabilizers are then added sequentially under constant mixing to ensure homogeneity. If essential oils are used, they are incorporated last, after the mixture has cooled to an appropriate temperature to preserve their integrity.

For the gel formulation, the emulsification process in an embodiment comprises the step of blending the mushroom extracts 203 with an aloe vera gel 300 base. This mixture does not include any oils or ingredients used in the salve. The process focuses on ensuring uniform distribution of the active compounds within the aloe vera base.

The incorporation of the emulsified products into the final formulation also varies between the salve and gel in accordance with embodiments. For the salve, the blended mixture is quickly transferred into containers while still warm and flowing easily. Safety seals are applied, and jars are closed. The containers are immediately placed in the refrigerator for 8-10 hours to cool and solidify the mixture before it has time to separate and settle at room temperature.

For the gel formulation, the incorporation process in an embodiment involves carefully mixing the aloe vera and mushroom extract blend to avoid introducing air bubbles. The final product is then stored in dark or amber bottles to prevent light destabilization.

This comprehensive preparation method ensures that the tattoo aftercare composition retains the maximum therapeutic potential of the medicinal mushrooms while providing a stable, effective product for both immediate healing needs and long-term maintenance of tattooed skin.

In accordance with an embodiment of the invention, the formulation consists of a tattoo glide. The tattoo glide formulation is designed specifically for use during the tattooing process, potentially distinct from aftercare products. In accordance with an embodiment, this specialized formulation is created to address the unique needs of the skin during the tattooing procedure.

The composition of the tattoo glide in an embodiment comprises a blend of ingredients each chosen for its specific properties and benefits. The base in an embodiment of the tattoo glide formulation comprises synthetic white beeswax pellets 202, which provide structure and help create a smooth consistency. Shea butter 200 is incorporated in an embodiment of the glide formulation for its ability to melt at body temperature, allowing for easy and gentle application over the skin during tattooing. Sweet almond oil and grape seed oil 204 in an embodiment of the glide formulation each serve as non-comedogenic carrier oils, ensuring the formulation doesn't clog pores or prevent the tattoo from breathing. These oils also contribute to the product's light texture and easy absorption. A key active ingredient in the glide formulation in an embodiment is Chaga liquid herbal supplement extract, which brings its unique healing and protective properties to the glide. In various other embodiments of the glide formulation, other mushrooms as described elsewhere herein are incorporated.

The benefits of the tattoo glide forming an embodiment of the invention are multifaceted, addressing several aspects of the tattooing process. Firstly, it provides lubrication during the process of applying a tattoo, reducing friction between the needle and the skin. This lubrication helps the needles move more effortlessly, reducing resistance and making the tattooing process more efficient while minimizing trauma to the skin. The reduced friction means less force is needed for the needle to penetrate the skin, potentially minimizing overall trauma and reducing the likelihood of excessive scabbing and prolonged healing times.

Secondly, the tattoo glide in an embodiment of the invention acts as a protective barrier. During tattooing, excess ink and blood can spread uncontrollably. The application of the glide helps prevent these fluids from spreading, keeping the tattoo area cleaner and more visible. This allows for more precise work and reduces the risk of infection. Some color artists may also apply the glide over colored areas that have already been tattooed as a barrier to prevent new colors from being absorbed by open pores, potentially resulting in a cleaner, less muddy tattoo.

The tattoo glide formulation in accordance with an embodiment specifically includes ingredients that contribute to the protective barrier function of the tattoo glide. The synthetic white beeswax pellets 202, present at 12 tablespoons per 56 oz batch in an embodiment, act as a base and binding agent, creating a smooth consistency that helps form a physical barrier on the skin surface. This barrier aids in preventing the spread of excess ink and blood during the tattooing process. The inclusion of 3⅓ cups of raw, unrefined shea butter 200 per batch in an embodiment further enhances the protective properties of the glide. Shea butter 200's ability to melt at body temperature allows it to spread evenly and form a thin, protective layer over the skin. This layer helps contain fluids within the tattooed area, keeping it cleaner and more visible for the artist. The non-comedogenic carrier oils, specifically 1.5 cups of sweet almond oil 201 and ¾ cup of grape seed oil 204 per batch in an embodiment, contribute to the barrier function while ensuring breathability. These oils help create a semi-occlusive layer that allows for some air and moisture exchange but protects the skin from external contaminants. This balance is crucial for maintaining an optimal environment for tattooing while preventing the absorption of unwanted substances. The addition of 12 ml of Chaga liquid herbal supplement extract per batch in an embodiment not only provides healing and protective properties but also contributes to the overall barrier function. The high concentration of melanin and other compounds in Chaga help to create an additional protective layer, potentially reducing the risk of infection and supporting the skin's natural defense mechanisms during the tattooing process.

An embodiment of the formulation comprises the following percentage ranges for key ingredients: synthetic white beeswax pellets 202 at 5-10% by weight, shea butter 200 at 30-40% by weight, sweet almond oil 201 at 15-25% by weight, grape seed oil 204 at 5-15% by weight, and Chaga liquid herbal supplement extract at 0.5-2% by weight.

In an embodiment providing a gel formulation, the composition comprises Chaga tincture 303 at 2-5% by weight, Turkey tail tincture 302 at 2-5% by weight, Red Reishi tincture 301 at 2-5% by weight, and an aloe vera gel mixture 300 comprising 85-94% by weight of the total composition.

In alternative embodiments, the formulation may include additional or substitute mushroom extracts 203 such as Shiitake, Cordyceps, Maitake, Agaricus Blazei, Oyster, Porcini, Enoki, Matsutake, Wood Ear, King Trumpet, and White Button, each selected for their unique healing, anti-inflammatory, antimicrobial, and antioxidant properties that can contribute to tattoo aftercare and skin health. These alternative mushroom extracts can be incorporated into the formulation within similar percentage ranges as the primary mushroom extracts, in an embodiment between 0.5-5% by weight, depending on the specific properties and potency of each mushroom species.

In various embodiments, the formulation aids in moisture retention. Skin can dry out quickly during the tattooing process, especially with repeated wiping and the use of alcohol as a disinfectant. The tattoo glide formulation embodiment in particular helps maintain moisture on the skin, which is crucial because hydrated skin tends to be more pliable and less prone to irritation. This moisture retention also helps prevent micro-tears on the epidermis of the skin.

Lastly, the tattoo glide formulation embodiment contributes to ink saturation. By minimizing friction and maintaining skin moisture, the glide helps the ink settle more uniformly into the skin. This can result in more vibrant and consistent colors in the finished tattoo.

By addressing these key aspects of the tattooing process, the tattoo glide formulation offers a comprehensive solution that supports both the tattoo artist's work and the client's comfort and healing process. This specialized product demonstrates the invention's holistic approach to tattoo care, extending beyond aftercare to include products that enhance the tattooing process itself.

The inclusion of Chaga extract in the formulation in accordance with various embodiments provides additional benefits. Its anti-inflammatory properties can help reduce redness and irritation during the tattooing process, while its antimicrobial properties may help keep the area clean. The antioxidants in Chaga may also contribute to easier healing of the tattooed area.

In accordance with an embodiment of the formulation, the composition promotes rapid healing by stimulating the activation of macrophages, neutrophils, natural killer (NK) cells, and lymphocytes. This immune system activation is crucial for efficient wound healing and reducing the risk of infection in newly tattooed skin. Additionally, the β-glucans present in the mushroom extracts 203 directly increase the synthesis of types I and III collagen, stimulating collagen regeneration and accelerating the wound healing process.

To address the risk of infection, an embodiment further comprises non-comedogenic carrier oils such as grapeseed oil and tea tree oil. These oils have natural antiseptic properties and are high in vitamins A and C, which help prevent infection while keeping the skin hydrated and healthy. The formulation allows the tattooed skin to breathe properly, unlike traditional petroleum-based products that can create an occlusive barrier and potentially trap bacteria against the skin.

The composition in an embodiment formulated as a tattoo aftercare topical composition is designed to be applied approximately 48-72 hours after the tattooing process, once the initial dressing is removed. It can be used 2-3 times daily or as needed to maintain hydration and promote healing. This application schedule ensures that the tattooed skin receives consistent support throughout the critical healing phase.

Furthermore, an embodiment formulated as a tattoo aftercare topical composition addresses the long-term care of tattoos by incorporating UV protective qualities. The high melanin content naturally present in the Chaga mushroom extract offers a layer of protection against solar radiation, helping to maintain the vibrancy of the tattoo over time and combat the natural degradation that occurs with prolonged UV exposure. This feature is particularly valuable as it extends the utility of the invention beyond mere hydration and healing, addressing a significant gap in current tattoo aftercare products.

Various embodiments of the present invention comprise a blend of medicinal mushroom extracts 203, in an exemplary embodiment Chaga, Lion's Mane, Turkey Tail and Reishi, each chosen for their distinct healing properties and synergistic effects in tattoo aftercare.

Chaga mushroom extract is rich in antioxidants such as polyphenols, flavonoids, and melanin providing benefits to the composition in various embodiments. These compounds help protect the tattooed skin from oxidative stress caused by free radicals, environmental pollutants, and UV radiation. The high melanin content in Chaga also provides natural UV protection, which is crucial for maintaining tattoo vibrancy and preventing premature fading. Additionally, Chaga's anti-inflammatory properties help reduce swelling, redness, and pain associated with the tattooing process.

Lion's Mane mushroom extract contributes neuroprotective and anti-inflammatory properties to the formulation providing benefits to the composition in various embodiments. These characteristics support nerve regeneration and aid in pain management during the tattoo healing process. The anti-inflammatory effects of Lion's Mane help reduce swelling and redness, promoting faster healing of the tattooed skin.

Reishi mushroom extract provides immune-boosting and anti-inflammatory properties to the composition providing benefits to the composition in various embodiments. It contains polysaccharides and beta-glucans that help the skin retain moisture and regenerate its natural barriers. Reishi also stimulates collagen production, which improves skin elasticity and firmness, contributing to the overall healing process.

The synergistic effect of these mushroom extracts 203 in various embodiments is achieved through their combined action on various aspects of wound healing and skin protection. Together, they stimulate the activation of macrophages, neutrophils, natural killer (NK) cells, and lymphocytes, enhancing the body's immune response and expediting the natural healing process. The combination of their anti-inflammatory, antioxidant, and immune-boosting properties creates a comprehensive solution for tattoo aftercare that addresses both immediate healing needs and long-term skin health.

An embodiment of the present invention comprises an extraction process that maximizes the bioavailability of active compounds found in Chaga, Lion's Mane, Turkey Tail and Reishi mushrooms. This process involves a dual-phase extraction method that combines both hot water and ethanol extractions, ensuring a full spectrum of healing compounds is captured.

The extraction process begins with a careful selection of high-quality mushrooms, which are then prepared for extraction. The dual-phase extraction method is employed to ensure that both water-soluble and heat-sensitive compounds are effectively extracted from the mushrooms. This method is particularly important when working with mushrooms that contain a diverse range of bioactive compounds, such as Reishi, Chaga, Lion's Mane and Turkey Tail mushrooms.

The first phase of the extraction process involves soaking finely ground mushrooms in high-proof grain alcohol. This alcohol extraction helps to break down and dissolve the water-soluble compounds in the mushrooms, such as polysaccharides and triterpenes. The process typically takes several weeks, with occasional shaking or stirring to ensure thorough extraction.

The second phase involves boiling the alcohol-extracted mushrooms in hot water to extract the heat-sensitive compounds, such as beta-glucans and other immune-boosting compounds. This hot water extraction usually takes several hours on low heat, with the water being boiled down to a concentrated liquid.

Once both extractions are complete, the alcohol and water extracts are combined to create a potent extract that contains a wide range of beneficial compounds from the mushrooms. This dual extraction method is used to ensure that all the medicinal properties of the mushrooms are captured and preserved in the final product. The process is carefully controlled to maintain the integrity of the sensitive compounds and to prevent degradation. This extraction process associated with an embodiment of the invention maximizes the bioavailability of the active compounds, ensuring their efficacy in the final product. To ensure a stable and homogenous mixture, an embodiment employs a novel emulsification technique. This technique is critical for maintaining the efficacy of the active ingredients throughout the product's shelf life.

An embodiment of the present invention utilizes a slow simmering method to extract chitin and chitosan from mushroom cell walls, ensuring the bioavailability of these crucial components. This method involves a careful process of breaking down the proteins in the mushroom walls to release their beneficial properties. The slow simmering technique is essential for effectively extracting these compounds, as it allows for a more thorough breakdown of the mushroom cell structure compared to simple dehydration and grinding. This water-soluble extraction method is critical for the formulation in accordance with an embodiment, as it allows these components to be easily incorporated into the tattoo aftercare product and readily absorbed by the skin, maximizing their wound-healing and skin-fortifying properties.

The extraction process begins with the mushrooms being placed in water and heated at a low temperature for an extended period. This gentle heating process allows for the gradual breakdown of the cell walls, releasing the chitin and chitosan into the water. The slow simmering method is crucial because it preserves the integrity of these delicate compounds, which could be damaged or rendered less effective by more aggressive extraction techniques. This method ensures that the chitin and chitosan are extracted in their most bioavailable form, making them readily accessible for absorption by the skin when applied in the tattoo aftercare formulation. In contrast to simple dehydration and grinding, which may only break down the mushroom structure physically, the slow simmering method allows for a more complete extraction of the beneficial compounds. When mushrooms are merely dehydrated and ground, many of the valuable components remain trapped within the cell walls and are not properly harnessed for use by the body.

The emulsification process in embodiments is associated with two distinct formulations: a salve and a gel. For the salve, the carrier oils, waxes, and butters are gently heated and slowly combined to create a uniform base. The mushroom extracts 203, vitamins, emollients, emulsifiers, and stabilizers are then added sequentially under constant mixing to ensure homogeneity. If essential oils are used in the salve, they are incorporated last, after the mixture has cooled to an appropriate temperature to preserve their integrity.

In embodiments comprising a gel formulation, the process involves blending the mushroom extracts 203 with an aloe vera gel 300 base. This mixture does not include any oils or ingredients used in the salve. The gel preparation focuses on incorporating the mushroom extractions into the aloe vera base, ensuring a uniform distribution of the active compounds.

Both processes ensure that all components are evenly distributed and remain stable in their respective final products. The separation of the oil-based salve and the water-based gel formulations allows for different application methods and textures, catering to various preferences and specific needs in tattoo aftercare.

The manufacturing process in an exemplary embodiment is designed to be compatible with standard cosmetic production equipment, ensuring that it can be easily and economically scaled to meet market demand. In accordance with an embodiment, production is conducted in a GMP (Good Manufacturing Practice) certified laboratory, which ensures the highest standards of quality and safety throughout the manufacturing process. This GMP certification guarantees that the product is consistently produced and controlled according to quality standards appropriate for its intended use and as required by regulatory agencies. Quality control measures are in place at every stage of production, from raw material sourcing to final packaging, to ensure that each batch of the product meets high standards. The use of a GMP certified facility further enhances these quality control measures, providing additional assurance of product safety, consistency, and efficacy.

The manufacturing process associated with an exemplary embodiment of the present invention is directed to either of two distinct formulations: a salve and a gel. Both are produced using standard cosmetic production equipment in a GMP certified laboratory, ensuring quality, safety, and scalability.

Embodiments of the invention comprise two distinct formulations: a salve and a gel, each tailored to address specific aspects of tattoo aftercare. For the salve formulation, in accordance with an embodiment comprises Chaga Mushroom Extract, Turkey Tail Extract, Red Reishi Mushroom Extract 301, White Beeswax pellets 202, Shea butter 200, Grapeseed Oil, Sweet Almond oil 201, and Tea Tree Oil. In accordance with an exemplary method preparation of a 50 oz batch of the salve 100 in an embodiment, the preparation method for the salve begins with melting the beeswax pellets 202 in a double boiler over medium heat 101. Shea butter 200 is added 102 and mushroom extracts 203 are then added 103 while mixing thoroughly. The oils (grapeseed, sweet almond, and tea tree) are incorporated into the mixture 104. The entire mixture is then transferred to a blender for thorough blending 105. While still warm and flowing easily, the blended mixture is quickly transferred into containers. Safety seals are applied and jars are closed. The containers are immediately placed in the refrigerator for 8-10 hours to cool 106 and solidify the mixture before it has time to separate and settle at room temperature.

In an embodiment, the gel formulation comprises Chaga tincture 303, Turkey tail tincture 302, Red Reishi Tincture 301, and an Aloe Vera Gel Mixture 300 composed of various beneficial ingredients. In accordance with preparation of a 2 oz batch, the preparation method for the gel involves blending the aloe vera mixture with the mushroom tinctures. This process is done carefully to avoid introducing air bubbles. The final product is stored in dark or amber bottles to prevent light destabilization.

Both gel and salve formulations in accordance with an embodiment utilize an extraction process that maximizes the bioavailability of active compounds from the mushrooms, ensuring the efficacy of the final product. This extraction process involves a dual-phase method combining both hot water and ethanol extractions to ensure a full spectrum of healing compounds is captured from each mushroom species. The specific ratios and preparation methods for each formulation are designed to optimize the healing, moisturizing, and protective properties of the ingredients, addressing the unique needs of tattooed skin in different stages of the healing process.

The salve formulation in an embodiment is designed to be a slower-absorbing balm for application on fresh tattoos. Its composition allows for prolonged hydration and acts as a physical barrier between the tattooed skin and environmental contaminants. The gel formulation, on the other hand, is designed to be a quick-absorbing and soothing product that can be used on even the most delicate skin. It is light and refreshing, making it suitable for application over larger surface areas.

The compositions and preparation methods for various embodiments comprising salve and gel formulations as described herein ensure that embodiments of the present invention provide a comprehensive and effective solution for tattoo aftercare, addressing both the immediate healing needs of fresh tattoos and the long-term maintenance requirements of healed tattoos. The use of natural, non-comedogenic ingredients in such formulations ensures that the products are suitable for all skin types and do not clog pores or prevent the tattoo from breathing.

For the salve formulation in an embodiment, medicinal mushroom extracts 203 (Chaga, Lion's Mane, Turkey Tail, and Reishi) are prepared using a proprietary dual-phase extraction method, combining hot water and ethanol extractions to capture a full spectrum of healing compounds. The extracted compounds are combined to create a potent base. Non-comedogenic carrier oils are gently heated and slowly combined with the mushroom extract base using standard mixing equipment. Emollients, emulsifiers, and stabilizers are added sequentially under constant mixing, using high-shear mixers or homogenizers to achieve the desired consistency and ensure a stable, homogenous mixture. If included, essential oils are incorporated last, after the mixture has cooled to an appropriate temperature, preserving the integrity of the volatile compounds.

For the gel formulation in an embodiment, the mushroom extracts 203 are blended with an aloe vera gel 300 as a base, without incorporating any oils or ingredients used in the salve. The process focuses on ensuring uniform distribution of the active compounds within the aloe vera base.

In accordance with embodiments, formulations undergo rigorous quality control measures at every stage of production, from raw material sourcing to final packaging. The use of a GMP certified facility ensures that each batch meets high standards, maintaining consistency, quality, and efficacy across all production runs.

The versatility of the formulations in accordance with various embodiments allows for modification and adaptation into various forms such as creams, lotions, gels, or balms, achieved through adjustments in ingredient ratios and the use of appropriate mixing and processing equipment common in cosmetic manufacturing.

The unique combination of medicinal mushroom extracts 203 in various formulations in embodiments provides ongoing support for skin health and tattoo preservation. The high melanin content in Chaga mushroom extract offers natural UV radiation protection, critical for maintaining tattoo vibrancy over time and preventing premature fading due to sun exposure.

The antioxidant properties of the mushroom extracts 203, particularly the polyphenols, flavonoids, and melanin found in Chaga, continue to protect the tattooed skin from oxidative stress caused by free radicals and environmental pollutants long after the initial healing phase in an embodiment directed to tattoo aftercare. This ongoing protection helps maintain the skin's overall health and, consequently, the clarity and vibrancy of the tattoo.

The extraction and preparation method associated with embodiments of the invention, combined with the novel emulsification technique, results in a unique and effective tattoo aftercare product as an embodiment of the invention that maximizes the therapeutic benefits of the medicinal mushrooms while ensuring a stable and consistent formulation.

In an embodiment, the ratios and concentrations of each mushroom extract are carefully balanced to maximize their therapeutic effects. The formulation in an embodiment comprises:

Chaga Extract: 5-10% by weight
Lion's Mane Extract and/or Turkey Tail: 3-7% by weight
Reishi Extract: 3-7% by weight The unique combination and concentration of these mushroom extracts 203 in an embodiment of the present invention contribute to its effectiveness as a specialized tattoo aftercare solution, addressing the specific needs of healing tattooed skin while providing long-term benefits for tattoo preservation and skin health.

Various embodiments of the present invention comprise a comprehensive aftercare solution that addresses both the short-term healing needs and long-term maintenance of tattooed skin. This multi-functional approach sets it apart from traditional tattoo aftercare products by providing a single formulation that combines healing, moisturization, and UV protection.

For short-term healing, the formulation in an exemplary embodiment leverages the synergistic effects of Chaga, Lion's Mane, Turkey Tail and Reishi mushroom extracts 203. These extracts contain bioactive compounds such as beta-glucans, polysaccharides, and antioxidants that stimulate immune epithelial cells, support the extracellular matrix, and modulate cytokines and growth factors. This combination promotes rapid healing by enhancing the body's natural wound-healing processes, reducing inflammation, and minimizing the risk of infection in newly tattooed skin.

The composition in an exemplary embodiment also addresses long-term maintenance of tattooed skin through its unique formulation. The high melanin content in Chaga mushroom extract provides natural UV protection, which is crucial for preserving tattoo vibrancy and preventing premature fading over time. This feature allows the product to offer ongoing protection against UV damage, a common cause of tattoo degradation, without the need for additional chemical sunscreens.

The multi-functional aspects of the formulation in an exemplary embodiment are evident in its ability to simultaneously heal, moisturize, and protect tattooed skin. The mushroom extracts 203 stimulate collagen production, enhance immune response, and provide anti-inflammatory effects, all of which contribute to faster and more effective healing of tattooed skin. The inclusion of non-comedogenic carrier oils such as grapeseed oil and tea tree oil, or with aloe vera gel 300, provides essential hydration to the skin without clogging pores. This allows the skin to breathe properly during the healing process while maintaining optimal moisture levels. The natural UV protective qualities derived from the Chaga mushroom extract offer a layer of defense against solar radiation, helping to maintain tattoo vibrancy and prevent fading. This feature is particularly valuable as it addresses both short-term protection during the healing phase and long-term preservation of tattoo quality.

By combining these elements in a single formulation, an exemplary embodiment of the present invention provides a comprehensive solution that supports the entire lifecycle of a tattoo, from initial healing to long-term care. This multi-functional approach not only simplifies the aftercare process for users but also ensures consistent and effective care for tattooed skin over time.

The formulation in an embodiment is designed to be applied throughout all stages of the tattoo lifecycle, starting initially via a glide formulation during the tattoo application process, and subsequently as a tattoo aftercare formulation as a gel or salve in an embodiment at any point from soon after the application of the formulation through approximately 48-72 hours after the tattooing process, and continuing for ongoing maintenance. This versatility allows the product to adapt to the changing needs of tattooed skin, from the initial healing phase to long-term preservation, providing a continuous and comprehensive care solution.

Various embodiments of the present invention comprise significant UV protection properties deriving from the inclusion of mushrooms as described herein, which are crucial in the context of tattoo care. This feature addresses a critical gap in traditional tattoo aftercare products and provides a comprehensive solution for both short-term healing and long-term tattoo preservation.

The UV protective qualities of the composition are primarily derived from the Chaga mushroom extract, which contains a high concentration of melanin. Melanin is a natural pigment known for its ability to absorb harmful UV rays, effectively acting as a natural sunscreen. This property is particularly valuable in tattoo aftercare, as it provides a layer of protection against solar radiation without the need for additional chemical sunscreens, which can be problematic for healing tattoos.

In the context of tattoo care, the present inventor recognizes that UV protection is of paramount importance. Newly tattooed skin is especially vulnerable to UV damage, which can not only interfere with the healing process but also cause premature fading of the tattoo. Traditional aftercare instructions often advise avoiding sun exposure or using sunscreen, but this creates a dilemma as applying chemical sunscreens to fresh tattoos is not recommended due to potential irritation and interference with healing.

The Chaga extract in an exemplary embodiment provides a solution to this challenge by offering inherent UV protection. This natural UV barrier helps shield the tattooed area from the damaging effects of UV exposure during both the critical initial healing phase and long-term maintenance. This provides a critical benefit in the context of an embodiment, as it addresses the unique challenge of protecting fresh tattoos from sun exposure without the use of traditional sunscreens or other chemical compositions. Chaga mushrooms contain a high concentration of melanin, a natural pigment known for its ability to absorb harmful UV rays, effectively acting as a natural sunscreen. By incorporating this protection into the aftercare formulation, the invention addresses the need for UV protection without compromising the healing process or introducing potentially harmful chemicals to the tattooed skin.

The UV protective properties of the composition in an embodiment play a crucial role in maintaining tattoo vibrancy and preventing premature fading. UV radiation is one of the primary causes of tattoo degradation over time, as it can break down the ink particles and cause them to fade or change color. By providing a consistent layer of UV protection, an embodiment helps preserve the integrity of the tattoo ink within the skin.

This protective effect extends beyond the initial healing phase, offering long-term benefits for tattoo preservation. Regular use of the product in an embodiment comprising a tattoo aftercare formulation help maintain the clarity and vibrancy of tattoos, reducing the rate of fading and color distortion that often occurs with prolonged UV exposure. This feature is particularly valuable for individuals seeking to preserve the quality and appearance of their tattoos over extended periods.

Moreover, the UV protection provided by the Chaga extract complements the other healing and nourishing properties of the mushroom blend in the formulation. This synergistic effect not only protects the tattoo from UV damage but also supports overall skin health, contributing to better healing outcomes and long-term tattoo quality.

Traditional aftercare instructions often advise avoiding sun exposure or using sunscreen, but applying chemical sunscreens to fresh tattoos is not recommended due to potential irritation and interference with healing. The Chaga extract in an embodiment offers a solution to this challenge by providing inherent UV protection through its melanin content. This natural UV barrier helps shield the tattooed area from the damaging effects of UV exposure during both the critical initial healing phase and long-term maintenance, without compromising the healing process or introducing potentially harmful chemicals to the tattooed skin.

The inclusion of natural UV protection in an embodiment represents a critical aspect associated with embodiments in facilitating tattoo aftercare. An embodiment addresses the critical need for UV protection in tattoo care while avoiding the potential drawbacks of traditional sunscreens, thereby offering a more comprehensive and tailored solution for tattoo aftercare and long-term maintenance.

Embodiments of the present invention comprise medicinal mushroom extracts 203 as described herein that further contribute significantly to the different stages of wound healing, addressing the unique challenges of tattoo aftercare as recognized by the present inventor. While the mushroom extracts 203 do not directly contribute to blood clotting, they support the overall healing process by preparing the wound environment for subsequent stages. The anti-inflammatory properties of Chaga, Lion's Mane, Turkey Tail and Reishi mushrooms play a crucial role in this stage. These extracts help reduce swelling, redness, and pain associated with the tattooing process. The β-glucans present in the mushroom extracts 203 stimulate the activation of macrophages, neutrophils, natural killer (NK) cells, and lymphocytes, enhancing the body's immune response and expediting the natural healing process. During the proliferation stage, the mushroom extracts 203 significantly contribute to tissue growth and repair. The β-glucans from the mushrooms directly increase the synthesis of types I and III collagen, stimulating collagen regeneration and helping the wound healing process. Additionally, the polysaccharides and beta-glucans found in Reishi mushrooms help the skin retain moisture and regenerate its natural barriers, supporting the proliferation of new skin cells. In the final remodeling stage of wound healing, the mushroom extracts 203 continue to support the skin's recovery. The ongoing stimulation of collagen production, particularly by the Reishi extract, helps improve skin elasticity and firmness, contributing to the overall healing process and long-term skin health.

The role of beta-glucans, chitin, and chitosan from the mushrooms in enhancing fibroblast proliferation and collagen synthesis is crucial to the wound healing process in accordance with an embodiment. Beta-glucans, found in various mushroom extracts 203 utilized in accordance with various embodiments, stimulate the activation of macrophages and other immune cells, which in turn promote the proliferation of fibroblasts. Fibroblasts are essential for producing collagen and other components of the extracellular matrix, which are vital for wound healing and skin regeneration. Chitin and chitosan, components of mushroom cell walls, have been shown to enhance fibroblast proliferation and collagen synthesis, speeding up wound healing and fortifying the skin barrier. These compounds are extracted via a slow simmering method that breaks down the proteins in the walls of the mushroom and releases their properties. This water-soluble extraction method ensures that these beneficial components are properly harnessed and made bioavailable in the formulation.

The combination of these mushroom-derived compounds works synergistically to support the wound healing process. They not only stimulate the production of new collagen but also help in organizing the newly formed collagen fibers, which is crucial for proper wound closure and minimizing scarring. This is particularly important in the context of tattoo aftercare, where maintaining the integrity of the skin and the clarity of the tattoo are paramount. By incorporating these specific wound healing mechanisms, an embodiment of the present invention offers a comprehensive approach to tattoo aftercare that addresses both the immediate healing needs of freshly tattooed skin and the long-term health and appearance of the tattoo.

The medicinal mushroom extracts 203 of embodiments of the invention further play a crucial role in activating the body's immune response, specifically stimulating macrophages, neutrophils, natural killer cells, and lymphocytes. This immune system activation is essential for efficient wound healing and reducing the risk of infection in newly tattooed skin. The mushroom extracts 203, particularly from Chaga, Lion's Mane, and Reishi, contain immunostimulant compounds such as β-glucans, polyinosinic:polycytidylic acid, and lipopolysaccharide. These compounds are known to boost immune system activity. The β-glucans, in particular, play a significant role in stimulating the activation of macrophages, neutrophils, natural killer (NK) cells, and lymphocytes. Macrophages are recruited to the wound site as a mechanism of wound healing by the β-glucans present in the mushroom extracts 203. This recruitment is crucial for the initial stages of the healing process, as macrophages help clean up debris and foreign substances at the tattoo site. Neutrophils, which are among the first responders to the site of injury, are also stimulated by the mushroom extracts 203. These cells help remove debris, foreign substances, and microbes from the tattooed area, contributing to the prevention of infection and promotion of healing. Natural killer (NK) cells, part of the innate immune system, are activated by the mushroom extracts 203. While their primary function is typically associated with viral defense, their activation contributes to the overall immune response in the tattooed area. Lymphocytes, including T cells and B cells, are also stimulated by the mushroom extracts 203. These cells play a crucial role in the adaptive immune response, helping to recognize and remember specific pathogens, which is beneficial for long-term skin health and protection against potential infections. The activation of these immune cells by the mushroom extracts 203 contributes to various aspects of the wound healing process. They help in the removal of damaged tissue, promote the formation of new blood vessels (angiogenesis), and stimulate the production of growth factors necessary for tissue repair. Moreover, the immune system activation provided by the mushroom extracts 203 extends beyond the initial healing phase. The ongoing stimulation of immune cells contributes to the long-term health of the tattooed skin, potentially helping to maintain the clarity and vibrancy of the tattoo over time. By incorporating these immune-stimulating properties, an embodiment of the present invention offers a comprehensive approach to tattoo aftercare that not only addresses the immediate healing needs but also supports the long-term health and appearance of the tattooed skin.

The medicinal mushroom extracts 203 of embodiments of the invention facilitate potent antioxidant properties, particularly focusing on protecting tattooed skin from oxidative stress and environmental pollutants. The Chaga mushroom extract, a key component of the formulation in accordance with embodiments, is rich in antioxidants such as polyphenols, flavonoids, and melanin. These compounds play a crucial role in protecting the tattooed skin from oxidative stress caused by free radicals, environmental pollutants, and UV radiation. The high concentration of antioxidants in Chaga helps neutralize free radicals, which can damage skin cells and potentially affect the clarity and longevity of the tattoo. Reishi mushroom extract, another essential ingredient in the composition in an exemplary embodiment, contains polysaccharides and beta-glucans that contribute to the antioxidant properties of the formulation. These compounds help the skin retain moisture and regenerate its natural barriers, which is crucial for protecting against environmental stressors.

The antioxidant properties of the mushroom extracts 203 work synergistically to create a protective barrier against various forms of oxidative stress in accordance with embodiments. This protection is particularly important for tattooed skin, which is more vulnerable to damage during the healing process and requires ongoing care to maintain its appearance. By neutralizing free radicals and reducing oxidative stress, the antioxidants in the mushroom extracts 203 help prevent premature aging of the skin and maintain the vibrancy of the tattoo. This is especially beneficial in urban environments where exposure to pollutants and other environmental stressors is more prevalent.

Moreover, the antioxidant properties of the mushroom extracts 203 contribute to the overall healing process of the tattooed skin in accordance with embodiments. By reducing oxidative stress, they support the skin's natural repair mechanisms, potentially leading to faster healing and better long-term outcomes for the tattoo. The combination of these antioxidant-rich mushroom extracts 203 in an embodiment provides a comprehensive approach to protecting tattooed skin from both internal and external sources of oxidative stress, contributing to better healing outcomes and long-term preservation of tattoo quality.

An embodiment of the present invention comprises non-comedogenic carrier oils as a key component of its formulation, addressing the critical need for proper skin breathability during the tattoo healing process. Specifically, the composition incorporates grapeseed oil and tea tree oil, which are selected for their ability to moisturize without clogging pores and for their natural antiseptic properties. Grapeseed oil is included in a weight percentage of 5-10%, while tea tree oil is present in a weight percentage of 0.5-2%. These oils are chosen for their light texture and ability to be easily absorbed by the skin without leaving a greasy residue. Grapeseed oil, in particular, is high in Vitamin E and antioxidants, which boost levels of collagen and elastin in the skin, promoting healing and maintaining skin health. The use of these non-comedogenic carrier oils allows the tattooed skin to breathe properly during the healing process. This is crucial because tattoos need oxygen to heal effectively, and any barrier that prevents proper oxygenation can delay the natural cell turnover and healing processes. By allowing the skin to breathe, the formulation promotes faster healing and reduces the risk of complications such as infection or excessive scabbing. This aspect of an embodiment significantly differentiates it from occlusive, pore-clogging products commonly used in tattoo aftercare. Traditional petroleum-based products, such as Aquaphor, which are often recommended in the tattoo industry, tend to create a thick, impermeable barrier over the tattoo. While various exemplary embodiments aim to keep the tattoo moisturized, they often lead to over-moisturization due to their slow absorption rate.

The non-comedogenic formulation of exemplary embodiments allows for proper moisturization without compromising the skin's ability to breathe and heal naturally. This balanced approach ensures that the tattooed skin receives the necessary hydration and nourishment while maintaining optimal conditions for healing and preventing complications associated with occlusive products. By incorporating non-comedogenic carrier oils, an embodiment of the present invention offers a solution that addresses the shortcomings of traditional tattoo aftercare products, providing effective moisturization while promoting proper healing and reducing the risk of complications associated with pore-clogging formulations.

An exemplary embodiment of the present invention is formulated to be safe and suitable for all skin types, including sensitive skin, through its hypoallergenic and non-irritating properties. The composition is designed to be inert, non-toxic, and stable, with a very low probability of causing any adverse or allergic reactions. The hypoallergenic nature of the formulation is achieved through the careful selection of natural ingredients and the avoidance of common irritants often found in other aftercare products. The use of medicinal mushroom extracts 203, specifically Chaga, Lion's Mane, Turkey Tail and Reishi, provides a natural base for the composition that is well-tolerated by most skin types. These mushroom extracts 203 are known for their anti-inflammatory properties, which can help reduce skin irritation and sensitivity.

The non-irritating properties of the composition are further enhanced by the inclusion of aloe vera gel 300 in an embodiment, which serves as a hydrating and soothing agent. Aloe vera has been used for centuries to aid in wound healing, soothe small burns, and relieve generalized skin irritation. Its ingredients have been proven safe on all skin types and applications. The formulation's suitability for sensitive skin is also attributed to the use of non-comedogenic carrier oils such as grapeseed oil and tea tree oil. These oils are selected for their ability to moisturize without clogging pores, which is particularly important for sensitive and acne-prone skin. Grapeseed oil, in particular, is known for its light texture and high content of antioxidants, making it suitable for various skin types.

An embodiment avoids common irritants found in other aftercare products by excluding synthetic fragrances, preservatives, and other potential allergens that can exacerbate skin sensitivity. Instead, the formulation relies on natural ingredients with known skin-soothing properties. For instance, if scent variations are added, they use natural essential oils in minimal quantities to prevent potential skin irritation. Moreover, the composition in an exemplary embodiment is free from alcohol, which can sting on fresh tattoos and dehydrate the skin, a common issue with some existing tattoo aftercare products.

The absence of petroleum-based ingredients in an embodiment, which are often recommended in the tattoo industry but can lead to over-moisturization and complications in the healing process, further contributes to the formulation's suitability for sensitive skin. The safety and suitability of an embodiment for all skin types are also supported by its versatility in application. The composition can be adapted into various forms such as creams, lotions, gels, or balms, allowing for broader applications in skincare beyond tattoo aftercare and catering to different skin type preferences.

An exemplary embodiment of the present invention demonstrates significant versatility in its formulation, allowing it to be adapted into various forms such as creams, lotions, gels, or balms. This adaptability enhances the product's utility and broadens its potential applications in skincare beyond tattoo aftercare.

Embodiments of the invention comprise formulations for both salve and gel compositions, each with specific ingredients and preparation methods tailored to their unique properties and applications in tattoo aftercare. The salve formulation is designed to be a slower-absorbing balm for application on fresh tattoos. Its composition allows for prolonged hydration and acts as a physical barrier between the tattooed skin and environmental contaminants.

The specific ingredients for a 50 oz batch of the salve in an exemplary embodiment include Chaga Mushroom Extract, Turkey Tail Extract, Red Reishi Mushroom Extract 301, White Beeswax pellets 202, Shea butter 200, Grapeseed Oil, Sweet Almond oil 201, and Tea Tree Oil. The preparation method for the salve involves a series of steps including melting the beeswax pellets 202 in a double boiler, adding shea butter 200 and mushroom extracts 203 while mixing thoroughly, incorporating the oils, blending the mixture, and finally cooling it in the refrigerator to prevent separation. The gel formulation, on the other hand, is designed to be a quick-absorbing and soothing product that can be used on even the most delicate skin. The present inventors have recognized that it is light and refreshing, making it suitable for application over larger surface areas.

The specific ingredients for a 2 oz batch of the gel in an exemplary embodiment include Chaga tincture 303, Turkey tail tincture 302, Red Reishi Tincture 301, and an Aloe Vera Gel Mixture 300 composed of various beneficial ingredients. The preparation method for the gel involves blending the aloe vera mixture with the mushroom tinctures, mixing carefully to avoid air bubbles, and storing in dark or amber bottles to prevent light destabilization.

Both of the immediately above exemplary formulations utilize an extraction process that maximizes the bioavailability of active compounds from the mushrooms, ensuring the efficacy of the final product. The specific ratios and preparation methods for each formulation are designed to optimize the healing, moisturizing, and protective properties of the ingredients, addressing the unique needs of tattooed skin in different stages of the healing process.

The composition's versatility in accordance with embodiments stems from its selected blend of ingredients, including medicinal mushroom extracts 203, aloe vera gel 300, and non-comedogenic carrier oils. These components can be combined in different ratios and with additional ingredients to achieve various consistencies and textures suitable for different application methods and skin types.

In accordance with an exemplary embodiment, the formulation can be prepared as a cream by incorporating a higher proportion of emollients and stabilizers, resulting in a thicker consistency ideal for targeted application on tattooed areas. Alternatively, it can be formulated as a lotion with a higher water content, making it more suitable for larger areas or for users who prefer a lighter texture.

The gel formulation of an embodiment is designed to be quick-absorbing and soothing, making it suitable for use on even the most delicate skin. This light and refreshing gel can help soothe overworked skin and can be applied over larger surface areas, extending its utility beyond tattoo aftercare. The balm or salve formulation in an embodiment, on the other hand, is designed to be a slower-absorbing product that creates a protective barrier on the skin. This form is particularly useful for fresh tattoos, as it keeps the tattooed area hydrated for longer and protected from environmental contaminants.

This versatility in formulation allows an embodiment to cater to a wide range of skincare needs beyond tattoo aftercare. The composition's healing, moisturizing, and UV-protective properties make it suitable for various dermatological applications, including the treatment of minor skin abrasions, thermal, wind, sun or radiation burns, psoriasis, eczema and other forms of dermatological trauma.

The adaptability of the formulation also allows for customization based on individual preferences and specific skin conditions. For instance, the product can be adjusted to suit different climate conditions or seasonal changes, providing year-round skincare solutions.

Moreover, the versatility of the formulation extends to its potential use in a variety of skin care contexts. The combination of medicinal mushroom extracts 203, known for their anti-inflammatory and antioxidant properties, with skin-friendly carrier oils and aloe vera gel 300, creates a product that could be beneficial for general skin health maintenance, anti-aging treatments, and even as a complementary product in professional skincare routines.

An exemplary embodiment of the present invention is provided with recommendations for the application process and frequency of use, addressing both fresh and aging tattoos. The present inventors have recognized that application should begin approximately 48-72 hours after the tattooing process, once the dressing is removed. This timing allows for the initial healing process to begin while ensuring that the product is applied early enough to provide maximum benefits. For fresh tattoos, the product should be applied generously to the tattooed area in a thin layer, ensuring full coverage. The recommended frequency of application in an embodiment is 2-3 times daily or as needed to maintain hydration and promote healing. This frequent application during the initial healing phase helps to keep the tattooed skin moisturized, reduce inflammation, and protect against potential infections. The application process should continue as per the tattoo artist's aftercare instructions or until the skin is fully healed. This tailored approach allows for flexibility based on individual healing rates and the specific requirements of different tattoo styles and sizes.

For ongoing maintenance of both fresh and aging tattoos, the product can be used to keep the tattooed skin moisturized and protected from UV radiation. The frequency of application for long-term care can be adjusted based on individual needs and environmental factors. This flexibility in application frequency for long-term use ensures that the tattooed skin continues to receive the benefits of the formulation well beyond the initial healing phase.

The benefits of the product for fresh tattoos include expedited healing, reduced risk of infection, and minimized scarring or color fading. The unique combination of medicinal mushroom extracts 203 provides anti-inflammatory and antimicrobial properties that support the body's natural healing processes. Additionally, the formulation's ability to maintain proper skin hydration without over-moisturizing helps prevent complications such as scab formation and ink loss.

For aging tattoos, the product offers significant benefits in terms of long-term preservation and skin health. The high melanin content found in the Chaga mushroom extract provides ongoing UV protection, helping to prevent premature fading of the tattoo due to sun exposure. The antioxidant properties of the mushroom extracts 203 continue to protect the tattooed skin from oxidative stress and environmental pollutants, contributing to the overall health of the skin and the longevity of the tattoo's appearance. Furthermore, the formulation's ability in an embodiment to support collagen production and maintain skin elasticity benefits aging tattoos by helping to preserve the tattoo's shape and clarity as the skin ages. The ongoing moisturizing and skin barrier support provided by the product also helps to maintain the vibrancy and overall quality of the tattoo over time. By addressing both the immediate aftercare needs of fresh tattoos and the long-term maintenance requirements of aging tattoos, an embodiment offers a comprehensive solution for tattoo care throughout the life of the tattoo.

Furthermore, the polysaccharides and beta-glucans present in the Reishi mushroom extract contribute to long-term skin health by helping the skin retain moisture and regenerate its natural barriers. This continuous support for skin hydration and barrier function is essential for maintaining the tattoo's appearance and preventing issues such as dryness or flaking that could affect the tattoo's quality over time. The formulation's ability to stimulate collagen production, particularly through the Reishi extract, provides long-term benefits for skin elasticity and firmness. This ongoing support for skin structure helps maintain the tattoo's shape and clarity as the skin ages, contributing to the overall longevity of the tattoo's appearance.

The immune-boosting properties of the mushroom extracts 203 continue to benefit the skin long after the initial healing phase. By supporting the skin's natural defense mechanisms, the formulation helps protect against potential infections or irritations that could affect the tattoo's appearance over time.

An exemplary embodiment is intended for both initial aftercare and ongoing tattoo maintenance, with the recommendation that it can be used to keep the tattooed skin moisturized and protected from UV radiation as part of a long-term care routine. This dual-purpose approach ensures that the benefits of the formulation extend well beyond the initial healing phase, providing comprehensive care for the life of the tattoo.

An embodiment of the present invention demonstrates superior effectiveness compared to existing tattoo aftercare products in terms of healing time, infection prevention, and long-term tattoo preservation. The unique combination of medicinal mushroom extracts 203, particularly Chaga, Lion's Mane, Turkey Tail and Reishi, provides enhanced wound healing properties that can potentially reduce healing time compared to traditional aftercare products.

The formulation's antimicrobial properties, derived from compounds like beta-glucans and chitosan, offer improved infection prevention capabilities in an embodiment. Additionally, the invention's UV protective qualities, attributed to the high melanin content in Chaga extract, address the long-term preservation of tattoos by preventing premature fading due to sun exposure, a feature not commonly found in existing aftercare products. Unlike petroleum-based products that can lead to over-moisturization and delayed healing, this formulation promotes optimal healing conditions while maintaining proper skin breathability. The ongoing benefits of the formulation, including continued antioxidant protection and support for skin barrier function, contribute to superior long-term tattoo preservation compared to conventional aftercare solutions that often lack specific ingredients for active healing and long-term care.

By addressing both the immediate healing needs and the long-term maintenance requirements of tattooed skin, various embodiments provide a unique solution for tattoo aftercare. The composition's ability to provide ongoing protection, hydration, and support for skin health contributes to maintaining the vibrancy and clarity of tattoos over time, while also promoting overall skin health in the tattooed area.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

I claim:

1. A topical composition for use during or after the tattooing process, comprising:
   a mixture of medicinal mushroom extracts;
   synthetic white beeswax pellets;
   shea butter;
   sweet almond oil; and
   grape seed oil.

2. The topical composition of claim 1, wherein:
   the synthetic white beeswax pellets are present at 5-10% by weight;
   the shea butter is present at 30-40% by weight;
   the sweet almond oil is present at 15-25% by weight; and
   the grape seed oil is present at 5-15% by weight.

3. The topical composition of claim 1, wherein the medicinal mushroom extracts include at least one of Lion's Mane, Turkey Tail, and Reishi.

4. The topical composition of claim 1:
   the topical composition in the form of a salve, comprising
   a mixture of medicinal mushroom extracts including Chaga, Turkey Tail, and Red Reishi;
   synthetic white beeswax pellets;
   shea butter;
   grapeseed oil;
   sweet almond oil; and
   tea tree oil;
   wherein the composition is formulated to promote healing of previously tattooed skin.

5. The topical composition of claim 4, wherein the medicinal mushroom extracts are obtained through a dual-phase extraction method combining hot water and ethanol extractions.

6. The topical composition of claim 1,
   the topical composition in the form of a gel formulation,
   the mixture of medicinal mushroom extracts comprising:
      Chaga tincture;
      Turkey Tail tincture; and
      Red Reishi tincture;
      Lion's Mane tincture; and
   the topical composition further comprising:
      an aloe vera gel mixture;
   wherein the gel formulation is prepared by blending the aloe vera gel mixture with the mixture of medicinal mushroom extracts, mixing carefully to avoid air bubbles, and storing in dark or amber bottles to prevent light destabilization.

7. The topical composition of claim 1, wherein the mixture of medicinal mushroom extracts further comprises Chaga liquid herbal supplement extract.

8. The topical composition of claim 7, wherein the Chaga liquid herbal supplement extract is present at 0.5-2% by weight.

\* \* \* \* \*